United States Patent [19]
Richmond et al.

[11] Patent Number: 6,061,596
[45] Date of Patent: May 9, 2000

[54] METHOD FOR CONDITIONING PELVIC MUSCULATURE USING AN IMPLANTED MICROSTIMULATOR

[75] Inventors: Frances J. R. Richmond; Gerald E. Loeb, both of Kingston, Canada

[73] Assignee: Advanced Bionics Corporation, Sylmar, Calif.

[21] Appl. No.: 09/029,372

[22] PCT Filed: Nov. 20, 1996

[86] PCT No.: PCT/US96/18680

§ 371 Date: Feb. 25, 1998

§ 102(e) Date: Feb. 25, 1998

[87] PCT Pub. No.: WO97/18857

PCT Pub. Date: May 29, 1997

Related U.S. Application Data

[60] Provisional application No. 60/007,521, Nov. 24, 1995.

[51] Int. Cl.[7] .................................................. A61N 1/36
[52] U.S. Cl. .............................. 607/41; 607/40; 607/61
[58] Field of Search .............................. 607/39–42, 48, 607/53–57, 59, 61, 118, 138

[56] References Cited

U.S. PATENT DOCUMENTS

| | | |
|---|---|---|
| 3,727,616 | 4/1973 | Lenzkes ........................ 607/61 |
| 3,870,051 | 3/1975 | Brindley ....................... 607/41 |
| 4,102,344 | 7/1978 | Conway et al. ................ 607/40 |
| 4,406,288 | 9/1983 | Horwinski et al. ............. 607/41 |
| 4,607,639 | 8/1986 | Tanagho et al. ............... 607/41 |
| 4,612,934 | 9/1986 | Borkan ......................... 607/40 |
| 5,291,902 | 3/1994 | Carman ........................ 607/138 |
| 5,358,514 | 10/1994 | Schulman et al. ............ 607/61 |
| 5,562,717 | 10/1996 | Tippey et al. ................ 607/72 |
| 5,571,148 | 11/1996 | Loeb et al. ................... 607/57 |

Primary Examiner—Kennedy J. Schaetzle
Attorney, Agent, or Firm—Bryant R. Gold

[57] ABSTRACT

A system and method for conditioning pelvic muscle tissue for the purpose of treating urinary incontinence uses one or more tiny implantable stimulators (20)—termed "microstimulators"—implanted in or near certain pelvic structures so as to contact target muscle tissue. The microstimulators (20) are small enough to allow their implantation using a hypodermic needle (104). Once implanted, the microstimulators (20) are controlled using a controller (105, 106) and an appropriate coupling coil (102) that couples modulated radio frequency (RF) power into the microstimulators. A fitting station (110) facilitates adjusting the stimulus pattern and amplitude to best meet the needs of a given patient. Once fitted, electrical stimulation is thus provided to the target tissue in accordance with a specified externally-controlled exercise or other regime.

7 Claims, 4 Drawing Sheets

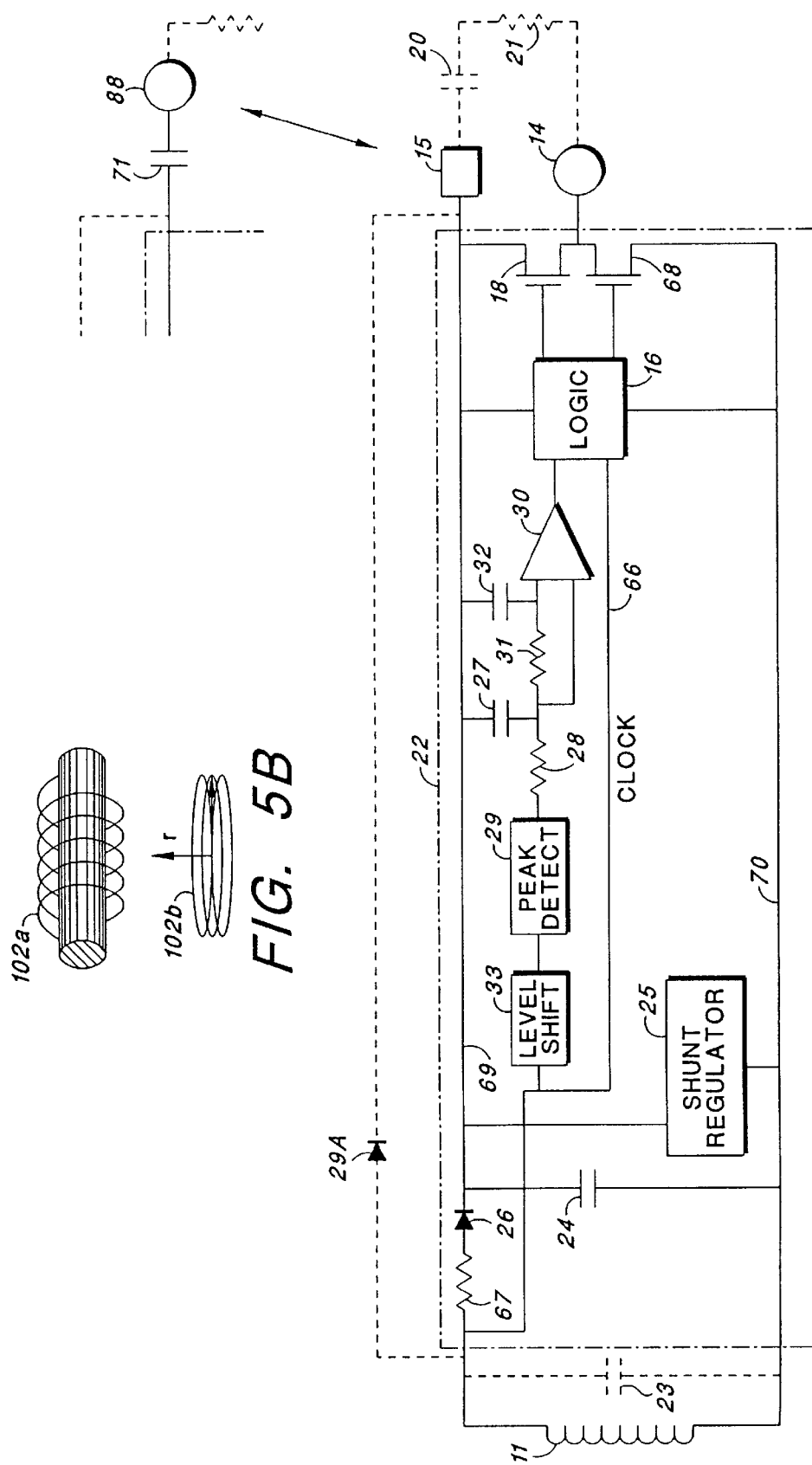

METHOD FOR CONDITIONING PELVIC MUSCULATURE USING AN IMPLANTED MICROSTIMULATOR

This application was filed in the United States under the provisions of 35 U.S.C. §371 based on international application PCT/US96/18680, filed Nov. 20, 1996; and claims the benefit of U.S. Provisional Application Ser. No. 60/007,521, filed Nov. 24, 1995.

BACKGROUND OF THE INVENTION

The present invention relates to a system and method for conditioning the pelvic musculature using one or more implanted microstimulators, and more particularly to a system and method for treating urinary incontinence using a radio-frequency-controlled implanted microstimulator.

Urinary incontinence is an enormous medical and social problem, affecting 8% of people in industrialized countries. Expenditures on its treatment are conservatively estimated to be over 10 billion dollars. Nevertheless, aggressive therapies for this condition are used to treat only a small part of the affected population, and much of the market is driven by the need for absorptive products rather than state-of-the-art devices.

Incontinence can be divided into at least three major categories of pathophysiology:

1. Overflow incontinence, which arises from a failure of the bladder to contract at all or adequately for substantial emptying, so that urine accumulates until it overflows. This commonly occurs in spinal cord injury.
2. Stress incontinence, which arises from weakness of the urethral sphincteric muscles, which are unable to stop the forceful expulsion of urine during transient increases in intra-abdominal pressure such as during coughing and lifting. This commonly occurs in women following childbirth and/or menopause.
3. Urge incontinence, which arises from spontaneous activity of the bladder and/or sphincteric muscles producing a compelling feeling that the bladder needs to be emptied even when it contains little urine. This afflicts both men and women and probably arises from a variety of poorly understood dysfunctional reflexes.

It is has been observed over the past 50 years or so that conditioning exercises of the pelvic musculature can produce a reduction of stress incontinence in a majority of women who undertake this treatment. Pelvic conditioning therapies could potentially assist a large proportion of the more than 6 million women affected by stress incontinence in the United States alone. However, such exercises have not proved easy for many women to perform by voluntary contraction of the relevant muscles. Thus, electrical stimulation has been used to force contraction of the relevant muscles, and thereby achieve the desired muscle conditioning exercises.

Prior art devices that provide electrical stimulation to condition the pelvic musculature are based on the use of transcutaneous electrical stimulators which exercise pelvic muscles using externally-controlled regimes. While these prior art transcutaneous devices, introduced into the vagina or anal canal, have proven to be effective, they are often disliked by patients because of the associated embarrassment and sanitary problems. Further, in addition to stimulating the motor nerves, transcutaneously applied electrical currents necessarily stimulate the sensory nerves of the overlying skin, producing unpleasant sensations. It is thus apparent that there is a need in the art for a system and/or method for achieving the benefits of electrical stimulation of the pelvic musculature without the attendant problems associated with transcutaneous devices.

Stimulation of the bladder, sphincter and/or adjacent pelvic musculature and cutaneous nerves may also cause a reduction in the spontaneous sensations and contractions associated with urge incontinence, which is often combined with stress incontinence. The neural mechanism is unclear, but is believed to relate to a general property of neural reflect pathways that they can drift into states of hypersensitivity or spasticity as a result of various nonspecific insults and dysfunctional patterns of usage. Electrical stimulation may give rise to inhibitory neural activity that breaks the cycle of spasticity during a particular bout of urge incontinence. Repeated application of such stimulation may permit the patient to resist inappropriate urges to empty the bladder, thereby rebuilding normal bladder capacity and reducing the frequency of sensation that the bladder needs to be emptied. Repeated electrical stimulation may also lead to a reduction in the hypersensitivity of the neural pathways responsible for spontaneous sensations and contractions and a concomitant reduction in the incidence and/or severity of bouts of urge incontinence. Hence, it is evident that improved methods and techniques for electrically stimulating the bladder, sphincter and/or adjacent pelvic musculature and cutaneous nerves is socially and medically desirable, and would produce enormous benefits for patients suffering from incontinence, particularly stress incontinence and urge incontinence.

In U.S. Pat. No. 5,199,430, issued to Creasey et al., there is disclosed an electrical assistive device and a method for electrical stimulation that is used to produce urination in patients who have lost voluntary control of the bladder (such as the overflow incontinence pattern described above).

In U.S. Pat. No. 4,739,764, issued to Gleason et al., a method is described for controlling bladder emptying through the electrical stimulation of peripheral nerves supplying the bladder wall and external urethral sphincter. The method disclosed by Gleason et al. includes two applications related to urinary dysfunction. First, the method is suggested to assist bladder emptying for patients who have lost the ability to urinate under volitional control. Second, the method is suggested to assist the patient who is incontinent by providing a means to stimulate the sphincter muscles electrically. Specifically, the method described stimulates identified nerve bundles by using epineural electrodes, and by providing moment-to-moment control of the urinary sphincter at the time that continence is sensed to be compromised. This differs from the approach taken by Applicants in the present application in that Applicants' invention stimulates using small implantable stimulators that are implanted in or near the pelvic floor muscles for the purpose of providing conditioning stimulation on a regular, ongoing schedule. Such ongoing conditioning then results in continence via the natural voluntary control available to the patient. In other words, while the '764 patent addresses the continence problem by attempting to control the urinary sphincter with electrical stimulation, the present invention addresses the continence problem by regularly conditioning the pelvic muscles with electrical stimulation so as to restore voluntary control to the patient.

SUMMARY OF THE INVENTION

The present invention addresses the above and other needs, particularly as such needs exist relative to stress incontinence and urge incontinence, by providing a system and method that uses one or more tiny implantable stimulators—termed "microstimulators"—implanted in or near certain pelvic structures so as to contact target muscle tissue, e.g., pelvic floor muscles, and then controls such microstimulators so that electrical stimulation is provided to the target tissue in accordance with a specified externally-controlled exercise or conditioning regime. As the target muscle tissue is conditioned in this manner, voluntary control of such muscle tissue is returned to the patient.

In accordance with one aspect of the invention, the microstimulators that form a key component of the therapy system are hermetically encapsulated, leadless electrical stimulators that are small enough (e.g., 2 mm diameter by 13 mm length) to be injected percutaneously (or otherwise implanted) into the patient's muscle tissue. Thus, they are sufficiently small and innocuous that they could be left in the patient permanently in the unlikely event of a device failure. Further, implantation, e.g., through a large hypodermic needle under local anaesthesia could be performed as an outpatient office procedure, avoiding the costs, inconvenience and risk of morbidity that are normally associated with major surgery.

In operation, the microstimulators used as part of the present invention receive power and digital addressing and command signals from an external transmitter coil and control box. Advantageously, unlike transcutaneous stimulators, the microstimulators are unobtrusive and require no repeated insertions into body orifices. By implanting the devices under the skin, uncomfortable sensations associated with cutaneous stimulation can be avoided. Further, the microstimulator may be activated during work or leisure activities without visible evidence to other individuals who may be near the patient, e.g., in the same room as the patient, thus increasing the convenience and acceptability of the therapy.

In accordance with another aspect of the invention, the implanted microstimulators are readily controlled using an external control box, or control unit, coupled to an external transmitting coil which inductively couples (or otherwise transmits) programming information to the implanted microstimulator(s). For example, the transmitting coil may be placed in a cushion on which the patient sits during treatment, or the transmitting coil may be sewn into the patient's clothing.

In accordance with an additional aspect of the invention, the implantable microstimulators are implanted in or near certain pelvic structures by a transvaginal or transcutaneous approach, and are externally-controlled to transmit the desired pattern of electrical stimulation directly to adjacent motor and/or sensory nerve branches without the inconvenience, discomfort and hygienic problems associated with transcutaneous stimulators.

In accordance with yet another aspect of the invention, the patient and/or medical personnel can experiment with or test different stimulation regimes in order to find the particular stimulation regime or therapy pattern that is both comfortable and effective.

BRIEF DESCRIPTION OF THE DRAWINGS

The above and other aspects, features and advantages of the present invention will be more apparent from the following more particular description thereof, presented in conjunction with the following drawings wherein:

FIG. 3 is a simplified embodiment of the electrical circuit, including the electronic control means, of a preferred implanted microstimulator;

FIG. 5B illustrates the types of coils that may be used with the stimulation system in order to practice the invention.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
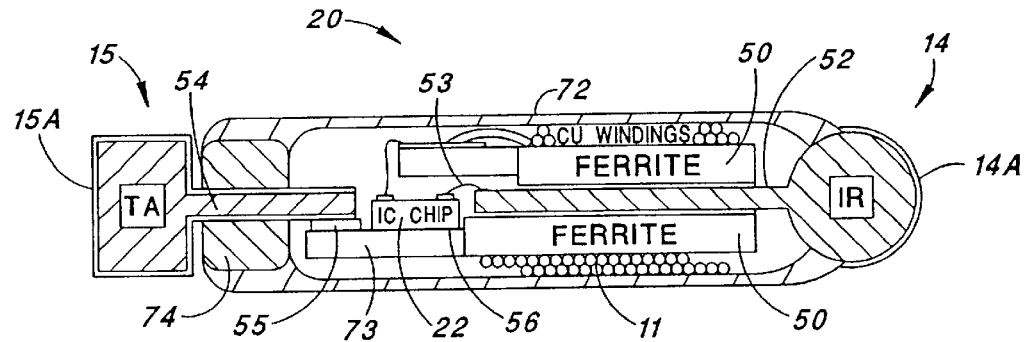
FIG. 1 is a cross-sectional view of one type of microstimulator that may be used with the present invention.

Referring first to FIG. 1, there is shown a microstimulator 20 of one type that may be used with the present invention. The microstimulator 20 is typically only about 10 to 15 mm in length, e.g., 13 mm, and comprises a quartz, glass, or ceramic tube or capsule 72, sealed at each end with a hermetic seal. For the embodiment shown in FIG. 1, a first electrode 14 protrudes out from one end of the glass capsule 72, and a second electrode 15 protrudes out from the other end of the capsule 72. Other embodiments may have the two electrodes 14 and 15 protruding out of the same end of the capsule 72. Such electrodes 14 and 15 are made from any suitable conductor, e.g., 0.025 to 0.150 mm diameter platinum-iridium wire.

In one embodiment, the electrode 14 may be made from iridium, and the electrode 15 may be made from tantalum. An anodized layer 15A covers the tantalum electrode 15, and an activated iridium layer 14A envelopes the iridium electrode 14. The use of a tantalum electrode 15 in combination with an iridium electrode 14 in this manner provides, by its structure, when immersed in body fluids, an electrolytic capacitor 20 having resistance 21. (See FIG. 3).

Inside of the glass capsule 72 is the electronic circuitry associated with the microstimulator 20. In particular, in accordance with one embodiment, the microstimulator 20 includes an integrated circuit (IC) chip 22, a ferrite core 50, and a coil 11 wound around the ferrite core 50. The IC chip 22 includes several logic and other circuits, including memory circuits.

All of the components and circuits within the microstimulator 20 are interconnected in circuit relationship so as to function as follows: (a) the coil 11 is inductively coupled to a modulated power signal that is generated external to the glass capsule 22; (b) the inductive coupling induces a modulated power signal in the coil 11; (c) the induced modulated power signal is rectified to provide operating power for the IC chip 22; (d) power from the rectified power signal charges a storage capacitor (which may be internal to the microstimulator 20, or formed by its electrodes); (e) the power signal is demodulated to extract an address word therefrom; (f) the extracted address word is compared to a preprogrammed microstimulator code stored in the microstimulator; and (g) if the extracted address code matches the preprogrammed microstimulator code, as determined by logic circuits included within the IC chip 22, the capacitor is discharged through the two electrodes 14 and 15 with an amplitude and pulse width determined by the incoming data stream. In this manner, then, the operation of the microstimulator, i.e., the selective discharging of its storage capacitor, is controlled through appropriate modulation of the power signal.

Details associated with the design, construction, and operation of different types of microstimulators 20 that may be used with the present invention are found in U.S. Pat. Nos. 5,324,316; 5,405,367; and/or 5,312,439, all of which patents are incorporated herein by reference.

Figure 2:
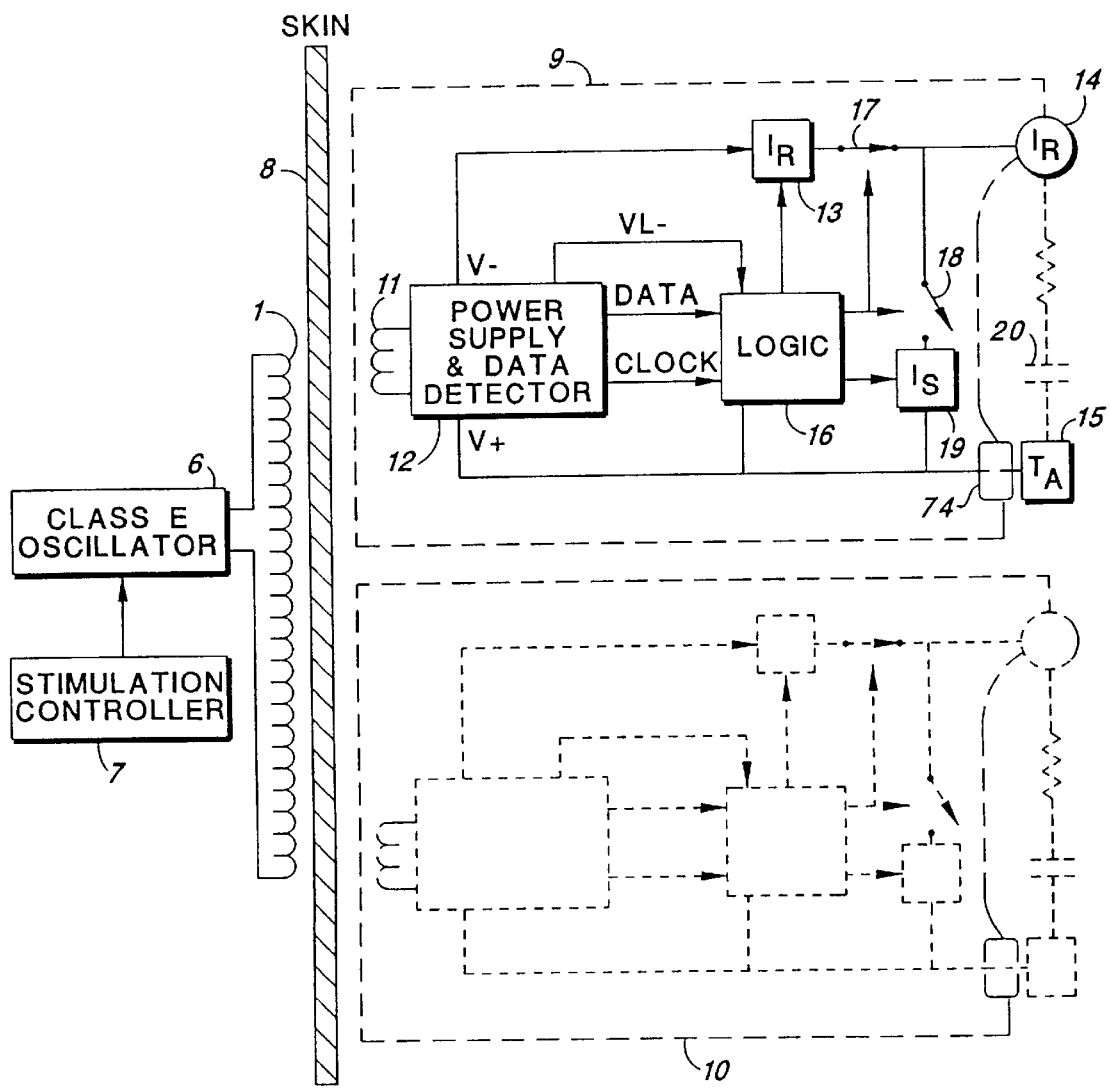
FIG. 2 is a block diagram illustrating the transcutaneous transmission of power and information to an implanted microstimulator.

FIG. 2 is a block diagram illustrating the transcutaneous transmission of power and information to the implanted microstimulator 20, while FIG. 3 is a simplified embodiment of the electrical circuit, including the electronic control means, of one type of implanted microstimulator. A thorough description of FIGS. 2 and 3 is found in U.S. Pat. No. 5,324,316, at col. 4, line 58, through col. 8, line 11, while additional details associated with the construction and operation of the microstimulator 20 are found throughout U.S. Pat. No. 5,324,316, and the other patents cited above.

With a working microstimulator 20 capable of being independently addressed from an externally-controlled transmitter to provide selective stimulation pulses between its two electrodes, it is possible using ingenuity and creativity to fashion a wide variety of stimulation systems and methods to fulfill various patient needs. The present invention, for example, utilizes one or more such microstimulator to particularly address the problems associated with stress incontinence and urge incontinence. In U.S. Pat. No. 5,571,148, also incorporated herein by reference, another application of utilizing a plurality of microstimulators is disclosed.

It is thus seen that the microstimulator 20 as described in the '316 patent (including all of its variations as described therein and in the other cited patents) represents an extremely versatile, and presently available, "building block". The present invention is directed to the application of the microstimulator technology to accomplish the desensitization, strengthening and/or general conditioning of the pelvic muscles and reflex pathways involved in maintaining continence, without encountering the limitations and problems inherent in the previously used approaches.

As indicated above, microstimulators are hermetically encapsulated, leadless electrical simulators that are small enough (e.g., 2 mm diameter by 13 mm length) to be injected (or otherwise placed) percutaneously into muscle tissue. The microstimulators receive their power and digital addressing and command signals from an external transmitter coil 102 driven by a control box 100 (FIG. 2).

Figure 4A:
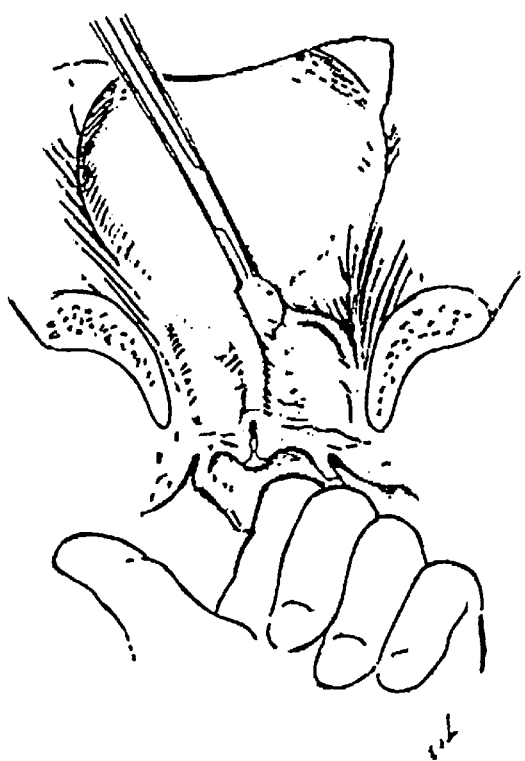
FIG. 4A shows a transvaginal approach for the implantation of a microstimulator, where the bladder neck is depicted as if viewed from inside the pelvis, and where the site of implantation of the microstimulator is being identified by digital exploration.
Figure 4B:
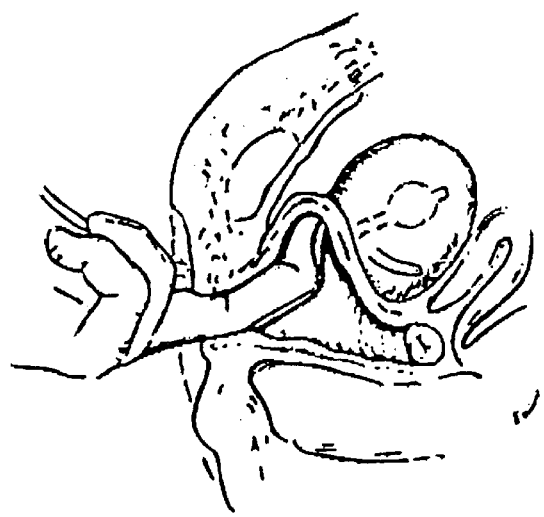
FIG. 4B shows the transvaginal approach for implantation of FIG. 4A, except that the site placement is viewed as if it were sectioned parasagittally.
Figure 5A:
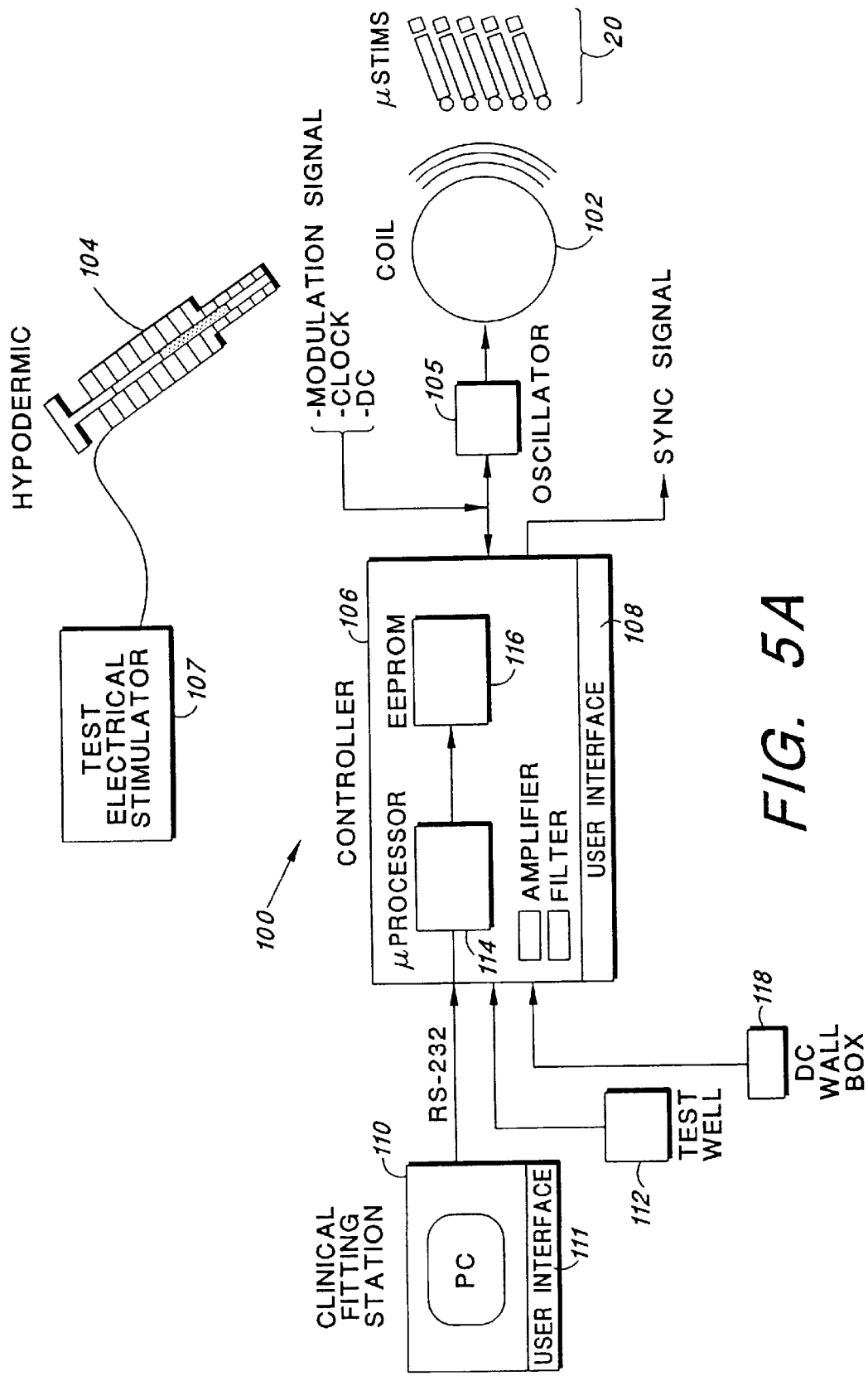
FIG. 5A is a block diagram that depicts the various elements that comprise a stimulation system and method which is made and practiced in accordance with the present invention.

In accordance with the present invention, one or more microstimulators 20, e.g., four microstimulators, are implanted in or near certain pelvic structures by a transvaginal or transcutaneous approach as suggested in, e.g., FIGS. 4A and 4B. The control unit or box 100, shown in block diagram form in FIG. 5, is used to externally control the microstimulators 20. The control unit is programmed to transmit the desired pattern of electrical stimulation directly to adjacent motor and/or sensory nerve branches without the inconvenience, discomfort and hygienic problems associated with transcutaneous stimulators.

The target tissue(s) in which the microstimulator(s) 20 are implanted will vary according to the specific pathophysiology of the patient. In most patients with stress incontinence, the microstimulators 20 are placed bilaterally in the striated perineal muscles that form a cuff around the anterior and lateral aspects of the urethra, preferably near the entry points of the muscle nerves. A single transmitting coil 102 (FIG. 5), e.g., placed in a cushion on which the patient sits during treatment, provides the power and command signals to all of the microstimulators 20 implanted in the general perineal region. The muscles are stimulated, i.e., conditioned, for 15–60 minutes (or other specified time period) each day using intermittent trains of electrical pulses sufficient in magnitude to result in direct or indirect activation of muscle fibers. As a result, the muscles and connective tissue are strengthened so that they develop more force when they contract around the urethra. Moreover, such conditioning adds bulk to the periurethral tissues to buttress the urethra.

In patients with urge incontinence, the microstimulators 20 may be implanted near other pelvic structures such as the bladder proper or under perineal skin. The patient is then given control of the control box or control unit 100 so that the patient initiates stimulation whenever the sense of urgency occurs. While clinical research will continue to establish the diagnostic criteria that identifies the most promising schedules and stimulation sites in various patients, the technology, general region of application, and the principles of treatment will be similar in all cases.

It should be noted that microstimulators offer several advantages over transcutaneous stimulators that are used increasingly for the treatment of stress incontinence. Compared to transcutaneous stimulators, implanted microstimulators are unobtrusive and require no repeated insertions in to body orifices. Thus, by implanting the devices under the skin, uncomfortable sensations associated with cutaneous stimulation can be avoided. Further, the microstimulators may be selectively activated during work or leisure activities without visible evidence to other individuals around the patient, thus increasing the convenience and acceptability of the therapy.

Further, microstimulators offer improvements over bulkier implantable systems that have been heretofore available for the stimulation of nerves and muscles. In prior systems, a relatively large receiver/power supply conveys electrical stimuli to the excitable tissues via long wire leads attached to electrodes that must be attached to or embedded in nerves or muscles. Such implantations require invasive surgical procedures that are both expensive and risky because of post-surgical complications. The multi-component implantable devices are also prone to failure because of lead breakage or receiver malfunction, and must then be removed surgically. Microstimulators, on the other hand, are totally self-contained units without long leads. They are sufficiently small and innocuous that they could be left in the patient permanently in the unlikely event of device failure. Because of their small size, microstimulators may be implanted through a large hypodermic needle 104 (FIG. 5) under local anaesthesia as an out-patient office procedure, thereby avoiding the costs, inconvenience and risk or morbidity that are normally associated with major surgery.

A system for conditioning muscle or nerve tissue of a patient with electrical stimuli in accordance with the present invention comprises: (1) at least one implantable microstimulator 20; (2) means for implanting the at least one microstimulator 20 in the patient so that it is in contact with target muscle or nerve tissue; and (3) an external transmitter that includes circuit components that allows it to generate a power and data signal that it sends to the at least one microstimulator. Because each microstimulator includes circuitry that responds to the power and data signal sent from the transmitter only when that particular microstimulator is addressed by the power and data signal, and when so addressed by providing an electrical stimulus of a prescribed energy level, it is thus possible for the at least one microstimulator to generate the prescribed pattern of stimulation pulses as controlled by the external transmitter.

The corresponding method for practicing the invention, in broad terms, thus includes the steps of: (a) implanting at least one implantable microstimulator so as to be in contact with tissue that needs to be stimulated (where the microstimulator includes electrical circuitry responsive to an externally applied power and data signal for generating a prescribed pattern of stimulation pulses); and (b) externally generating the power and data signal and transmitting it to the at least one microstimulator.

A block diagram is shown in FIG. 5 that depicts the various elements that comprise a stimulation system, and which are used in practicing a method, in accordance with the present invention. As seen in FIG. 5, such system includes one or more microstimulators 20. Four to six microstimulators are probably adequate for most incontinence problems, but any number of microstimulators can be used as needed. There must also, of course, be some means for implanting the microstimulators at the desired target tissue location. While any conventional implantation technique could be employed, a preferred approach is to use an insertion tool, such as a hypodermic needle 104 for percutaneous implantation of the microstimulator 20. In practice, a sharp trochar with a plastic sheath may be used for this purpose. The sharp trochar penetrates the skin to reach the targeted site, and the microstimulator 20 is then pushed through the sheath by a blunt plunger after the trochar is removed.

Additionally, before the trochar is removed, a conventional electrical stimulator 107 may be used to apply stimulation via the trochar to the tissue at the tip of the insertion tool in order to confirm that the stimulation site is a correct location in the perineal structures before the microstimulator is implanted through the sheath. This is an optional step, but a recommended step, because it will help assure that a correct stimulation site has been reached before actual implantation of the microstimulator.

A key element of the invention is the transmitting coil 102. The coil 102 may be contained within a cushion or garment means to be applied to the body in the vicinity of the implanted microstimulators. As illustrated in FIG. 5B, there are two types of coils. A first type is a cylindrical coil 102a, and this is the type of coil that is normally found within the microstimulator. A second type of coil 102b is a flat, or pancake, coil, and this is the type of coil that is typically used for the transmitter coil 102. For good inductive coupling between the two coils, it is preferred that the cylindrical coil of the implanted microstimulator be positioned a distance that is no greater than the radius r of the flat or pancake coil 102b. In general, it is preferable to have the coil 102 be of minimum size to reduce energy output. Of course, the size is governed by how many microstimulators are implanted, and their relative location to each other. Typical coil sizes for the coil 102 range from 15 cm to about 50 cm in diameter.

The coil 102 is coupled to oscillator and modulation circuitry 105, which circuitry is designed to produce electrical current in the coil 102 that results in a magnetic field which is coupled to the implanted coils of the microstimulator(s), which induces a voltage in the implanted coil. This induced voltage is the mechanism through which power and data are transmitted to the implanted microstimulators 20.

It should be noted that while inductive coupling is the preferred mode of transmitting power and data to the implant devices, other transmission techniques and/or media could be used to provide the requisite "link" between the implant device and the external control box, e.g., optical power/signal transmission, acoustic coupling, rf transmission, etc.

The oscillator/modulator 105 is driven by the control unit or box 106, e.g., a microprocessor 114 and EEPROM 116, and associated interface and signal processing circuitry (amplifiers, filters, etc.) that is programmed to produce the desired sequence of stimulation commands in response to a simple on/off switch activated by, e.g., the patient. Such on/off switch is made available to the patient through a suitable user interface circuit 108.

The system also includes a means for fitting the microstimulators 20 to a given patient. Such means is best realized using a personal computer (PC) 110 that has been programmed to allow a clinician to command the control unit 106 to test the microstimulator function in the patient, and with which the clinician can create and transmit to the control unit the desired stimulation pattern for muscle conditioning. The PC 110 may be any suitable PC, e.g., a 386-, 486- or Pentium-based PC of the type that is widely commercially available, having a keyboard 111 and/or other appropriate user interface devices (e.g., mouse, touch sensitive screen). The programming of such PC is straightforward (simply defining a stimulation pattern, and then programming the addresses of the individual microstimulators so that the stimulation pattern is realized) and may readily be done by a person of ordinary skill in the art given the teachings provided herein.

Thus, it is seen that the fitting station comprises a processor 110 having a user interface 111 that allows a user to temporarily select different stimulus patterns and stimulus amplitudes. The selected parameters are then formulated into appropriate commands by the controller 106, which commands are then sent to the implanted microstimulator 20 through the coil 102. In this manner, the selected stimulus pattern and stimulus amplitude may be tested for a desired result before finally selecting such stimulus pattern and stimulus amplitude for long term use by the system.

Thus, as part of the "fitting" process, the clinician, in cooperation with the patient, may experiment or run tests to determine the best stimulation pattern for the patient based on the effectiveness and comfort to the patient. Every patient may thus likely fashion a stimulation pattern that is unique to that patient, and which can be altered, as required, as time progresses and the conditioning of the muscle tissue allows normal continence to occur.

The invention also optionally includes a test well station or accessory 112 that allows the clinician to identify the address and test the function of microstimulators 20 immediately prior to implantation. This can be done, e.g., by recording the stimulus artifact produced by the microstimulator and capacitively coupling this artifact into recording electrodes that do not directly contact the microstimulator itself.

A DC wall box 118, if available in the area where the invention is being used, may be used to power the controller 106. Alternatively, commercially available AC power (e.g., at 110 Hz or 220 Hz) may power the controller 106 through a conventional AC-to-DC converter.

While the invention herein disclosed has been described by means of specific embodiments and applications thereof, numerous modifications and variations could be made thereto by those skilled in the art without departing from the scope of the invention set forth in the claims.

What is claimed is:

1. A method for conditioning pelvic muscle or nerve tissue for the treatment of urinary incontinence comprising:

implanting at least one leadless, tubular-shaped microstimulator (20) so as to be in contact with pelvic muscular or nerve tissue that needs to be stimulated for the treatment of urinary incontinence, said microstimulator including electrical circuitry responsive to an externally applied power and data signal for generating a prescribed pattern of stimulation pulses; and externally generating the power and data signal and transmitting it to the at least one microstimulator.

2. The method of claim 1 wherein the prescribed pattern of stimulation pulses defined by the applied power and data signal comprises a pattern of stimulation pulses that provides conditioning stimulation of the tissue on a regular, ongoing schedule, thereby allowing continence to occur via a natural voluntary control of the conditioned tissue.

3. A method for conditioning and training pelvic muscle tissue with electrical stimuli in order to treat urinary incontinence comprising:

implanting at least one implantable microstimulator in the patient so that exposed electrodes of the microstimulator are in contact with pelvic muscle or nerve tissue, said at least one microstimulator comprising a tubular case having exposed electrodes, and electrical circuitry hermetically sealed within said case and responsive to an externally applied power and data signal for generating at the exposed electrodes a prescribed pattern of stimulation pulses;

generating the power and data signal using an external control unit, and transmitting the power and data signal to the at least one implanted microstimulator so that the at least one implanted microstimulator generates the prescribed pattern of stimulation pulses as controlled by the external control unit, and conditions and trains pelvic muscle tissue in order to treat urinary incontinence.

4. The method of claim 3 further including:

coupling a fitting station to the implantable microstimulator through the external control unit, the fitting station having a user interface that allows a user to select different stimulus patterns and stimulus amplitudes;

selecting through the user interface a desired stimulus pattern and stimulus amplitude;

formulating the selected stimulus pattern and stimulus amplitude into appropriate command signals; and merging the command signals into the power and data signal that is transmitted to the at least one implanted microstimulator.

5. The method of claim 4 further including testing the selected stimulus pattern and stimulus amplitude for a desired result before finally selecting such stimulus pattern and stimulus amplitude for long term use.

6. The method of claim 5 wherein the step of implanting at least one implantable microstimulator comprises implanting at least four implantable microstimulators so that exposed electrodes of each microstimulator are in contact with pelvic muscle or nerve tissue.

7. A method for conditioning muscle or nerve tissue of a patient with electrical stimuli for the purpose of treating urinary incontinence comprising:

implanting a plurality of implantable, tubular-shaped, leadless, microstimulators, into the patient so that each is in contact with target pelvic muscle or nerve tissue;

coupling an external transmitter with the plurality of implantable microstimulators;

selecting a desired pattern of stimulation pulses to be applied to the muscle or nerve tissue;

generating a data signal within the external transmitter that is designed to cause a selected pattern of stimulation pulses to be generated by each of the plurality of microstimulators;

transmitting the data signal to each of the plurality of microstimulators;

receiving the data signal at each of the plurality of microstimulators;

generating stimulation pulses at each of the plurality of implanted microstimulators in response to the received data signal, wherein the stimulation pulses generated by the plurality of microstimulators combine to provide an overall pattern of stimulation pulses as prescribed by the external transmitter.

* * * * *